(12) United States Patent
Berlant

(10) Patent No.: US 6,486,198 B1
(45) Date of Patent: Nov. 26, 2002

(54) COMPOUNDS AND METHODS FOR THE TREATMENT OF POST TRAUMATIC STRESS DISORDER

(76) Inventor: Jeffrey Berlant, 2274 S. Swallowtail La., Boise, ID (US) 83706

(*) Notice: Subject to any disclaimer, the term of this patent is extended or adjusted under 35 U.S.C. 154(b) by 0 days.

(21) Appl. No.: 09/979,821

(22) PCT Filed: May 26, 2000

(86) PCT No.: PCT/US00/14593

§ 371 (c)(1),
(2), (4) Date: Mar. 11, 2002

(87) PCT Pub. No.: WO00/72841

PCT Pub. Date: Dec. 7, 2000

Related U.S. Application Data

(60) Provisional application No. 60/136,449, filed on May 28, 1999.

(51) Int. Cl.⁷ ..................... A61K 31/35; A61K 31/335; A61K 31/385
(52) U.S. Cl. ..................... 514/456; 514/459; 514/464; 514/465; 514/466; 514/517; 514/454; 514/455
(58) Field of Search ..................... 514/456, 459, 514/464, 465, 466, 517, 454, 455

(56) References Cited

U.S. PATENT DOCUMENTS

| | | | | |
|---|---|---|---|---|
| 4,513,006 A | * | 4/1985 | Maryanoff et al. | 514/23 |
| 5,384,327 A | * | 1/1995 | Costanzo et al. | 514/456 |
| 5,498,629 A | * | 3/1996 | Costenzo et al. | 514/439 |

* cited by examiner

*Primary Examiner*—Frederick Krass
(74) *Attorney, Agent, or Firm*—Christensen O'Connor Johnson Kindness PLLC

(57) ABSTRACT

The application relates to the use of topiramate and related sulfamates for the treatment and/or prophylaxis of post traumatic stress disorder (PTSD).

8 Claims, 1 Drawing Sheet

COMPOUNDS AND METHODS FOR THE TREATMENT OF POST TRAUMATIC STRESS DISORDER

CROSS-REFERENCE TO RELATED APPLICATIONS

This application claims the benefit of U.S. Provisional Application No. 60/136,449, filed May 28, 1999.

FIELD OF THE INVENTION

This invention relates to a methods for the treatment or prophylaxis of post-traumatic stress disorder (PTSD) using topiramate and related sulfamate derivatives and analogues, and the pharmacologically acceptable acid addition salts thereof, alone or in association with a pharmaceutically acceptable carrier.

BACKGROUND OF THE INVENTION

Chronic post-traumatic stress disorder (PTSD) is a difficult to treat condition. To date, the U.S. Food and Drug Administration has approved only one medication, sertraline, for the treatment of PTSD, and has limited the indication to women. Hypotheses on the etiology of PTSD have suggested that after exposure to traumatic events, limbic nuclei may become kindled or sensitized. Consequently, drugs known to have anti-kindling or anti-convulsant effects have been assessed as treatments for PTSD. (See Post RM et al., "Cocaine, kindling, and psychosis," *Am J Psychiatry* 133:627–634 (1976); Post RM et al., "Conditioning and sensitisation in the longitudinal course of affective illness," *Br J Psychiatry* 149:191–201 (1986); and Post RM et al., "Kindling versus quenching. Implications for the evolution and treatment of posttraumatic stress disorder," *Ann N Y Acad Sci* 821:285–295 (1997)). For example, carbamazepine may reduce reexperiencing and arousal symptoms, whereas valproate may reduce avoidance/numbing and arousal symptoms but not re-experiencing symptoms. (See Keck PE et al., "Valproate and carbamazepine in the treatment of panic and posttraumatic stress disorders, withdrawal states and behavioural dyscontrol syndromes," *J Clin Physchopharmacol* 12(suppl 1):36–41 (1992).)

The generic class of compounds of the following formula I:

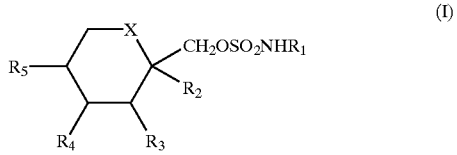

(I)

are structurally similar antiepileptic compounds that are highly effective anticonvulsants in animal tests (Maryanoff, B. E. et al., *Med. Chem.* 30:880–887 (1987); Maryanoff, B. E. et al., *Bioorganic & Medicinal Chemistry Letters* 3:2653–2656 (1993), McComsey, D. F. et al., *J. Org. Chem.* 1995). These compounds are covered by three U.S. Pat. Nos.: 4,5.13,006, 5,384,327 and 5,498,629. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. Faught et. al., *Epilepsia* 36 (S4) 33, 1995; S. K. Sachdeo et al., *Epilepsia* 36 (S4) 33, 1995), and is currently marketed for the treatment of simple and complex partial seizure epilepsy with or without secondary generalized seizures in Great Britain, Finland, the United States, Sweden and elsewhere, and applications for regulatory approval are presently pending or have been approved in over 50 countries throughout the world.

Compounds of Formula I were initially found to possess anticonvulsant activity in the traditional maximal electroshock seizure (MES) test in mice (Shank, R. P. et al., *Epilepsia* 35 450–460, 1994). Subsequent studies revealed that Compounds of Formula I were also highly effective in the MES test in rats. More recently topiramate was found to effectively block seizures in several rodent models of epilepsy (J. Nakamura et al., *Eur. J. Pharmacol.* 254 83–89, 1994), and in an animal model of kindled epilepsy (A. Wauquier et al., *Epilepsy Res.* 24, 73–77, 1996).

More recently, topiramate has been shown to have efficacy in the treatment of a broad range of seizure types in adults and children. (Faught E., "Efficacy of topiramate as adjunctive therapy in refractory partial seizures: United States trial experience," *Epilepsia* 38(suppl 1):24–27 (1997); Ben-Menachem E., "Clinical efficacy of topiramate as add-on therapy in refractory partial epilepsy: The European experience," *Epilepsia* 38(suppl 1):28–30 (1997); Reife R A et al., "Topiramate as adjunctive therapy in refractory partial epilepsy: Pooled analysis of data from five double-blind, placebo-controlled trials," *Epilepsia* 38(suppl 1):31–33 (1997); Rosenfeld W E et al., "Long-term experience with topiramate as adjunctive therapy and as monotherapy in patients with partial onset seizures: Retrospective study of open-label treatment," *Epilepsia* 38(suppl 1):34–36 (1997); Biton V., "Preliminary open-label experience with topiramate in primary generalized seizures," *Epilepsia* 38(suppl 1):42–44 (1997); Glauser T A, "Topiramate use in pediatric patients," *Can J Neurol Sci* 25:8–12 (1998); and Elterman R D et al., "A double-blind, randomized trial of topiramate as adjunctive therapy for partial-onset seizures in children. Topirarnate Y P Study Group.," Neurology 52:1338–1344 (1999)). The drug has an usually broad spectrum of pharmacological properties, with several proposed mechanisms of action. In addition to carbonic anhydrase inhibition, topiramate induces state-dependent blockade of voltage-gated Na+ channels, enhances GABAergic activity at GABAA receptors, blocks glutamate inhibition at kainate/AMPA receptors, and promotes protein phosphorylation of neuronal conductance channels. Topiramate thus combines several pharmacological properties of carbamazepine and valproate. In addition, U.S. Pat. No. 5,753,693 discloses that topiramate, and the sulfamate derivatives of formula I (above) are useful for the treatment of manic-depressive bipolar disorder (MDBD).

Recent preclinical studies on topiramate have revealed previously unrecognized pharnacological properties, which suggest that topiramate should be effective in treating post traumatic stress disorder (PTSD).

SUMMARY OF THE INVENTION

In accordance with the present invention, it has been found that topiramate and related sulfamate compounds of the following formula I:

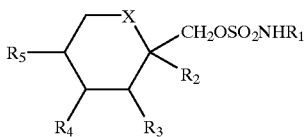

wherein X is O or CH$_2$, and R$_1$, R$_2$, R$_3$, R$_4$ and R$_5$ are as defined hereinafter, and the pharmacologically acceptable acid addition salts thereof, alone or in association with a pharmaceutically acceptable carrier, are useful in treating post traumatic stress disorder (PTSD). The compounds of the invention may also be used prophylactically to lessen the frequency and/or intensity of PTSD symptoms following a traumatic event.

This and other aspects of the invention will become apparent from the description of the invention which follows below.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
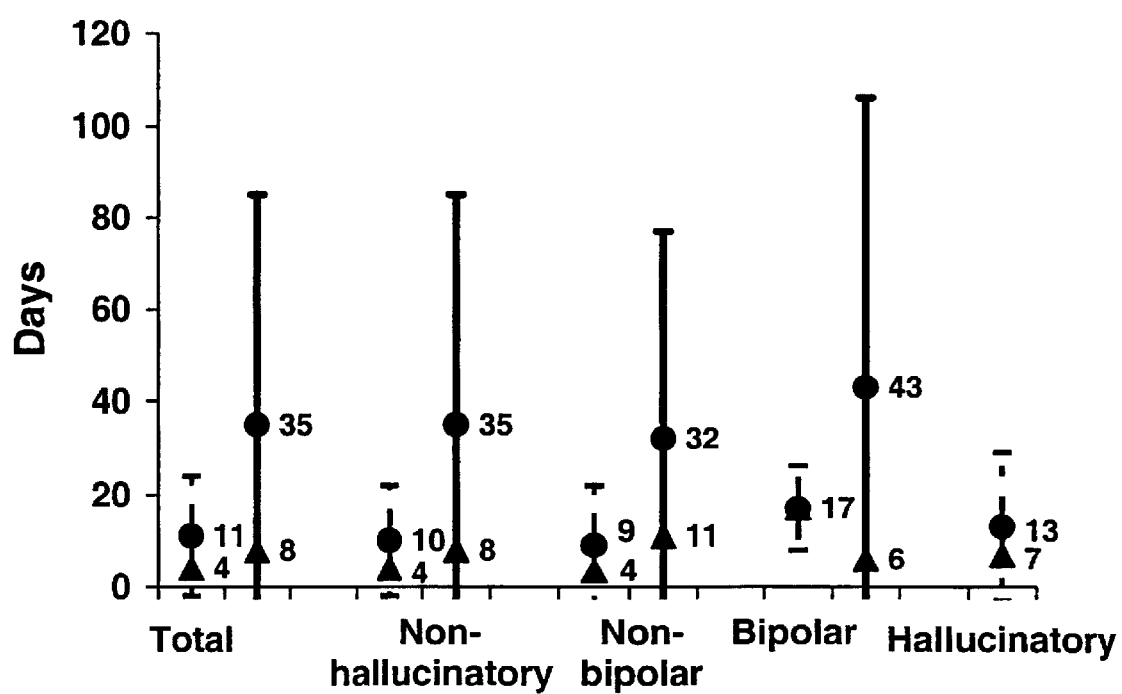
FIG. 1 is a graph showing the mean (solid black dots, "●") and median (solid black triangles, "▲") time to onset of response to topiramate by patient group for a partial response (shown as dashed bars) and for a full response (shown as solid bars), as described in Example 1.

In accordance with the present invention, methods are provided for the treatment and/or prophylaxis of post traumatic stress disorder (PTSD). Thus, in one aspect the present invention provides a method of inhibiting the symptoms of PTSD comprising administering to a patient in need of such treatment with an effective amount of a sulfamate compound of the following formula (I):

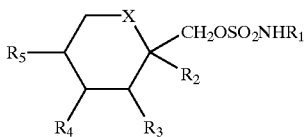

wherein

X is CH$_2$ or oxygen;

R$_1$ is hydrogen or alkyl; and

R$_2$, R$_3$, R$_4$ and R$_5$ are independently hydrogen or lower alkyl and, when X is CH$_2$, R$_4$ and R$_5$ may be alkene groups joined to form a benezene ring and, when X is oxygen, R$_2$ and R$_3$ and/or R$_4$ and R$_5$ together may be a methylenedioxy group of the following formula (II):

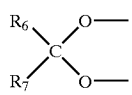

wherein R$_6$ and R$_7$ are the same or different and are hydrogen, lower alkyl or are alkyl and are joined to form a cyclopentyl or cyclohexyl ring;

and the pharmaceutically acceptable salts thereof;

either alone, or together with a pharmaceutically acceptable carrier.

In another aspect of the invention, a patient is first determined to be suffering from post traumatic stress disorder, and then the patient is treated by administering an amount of a compound of the invention effective to modulate the symptoms of the disorder, as set forth herein.

R$_1$ in particular is hydrogen or alkyl of about 1 to 4 carbons, such as methyl, ethyl and isopropyl. Alkyl throughout this specification includes straight and branched chain alkyl. Alkyl groups for R$_2$, R$_3$, R$_4$, R$_5$, R$_6$ and R$_7$ are of about 1 to 3 carbons and include methyl, ethyl, isopropyl and n-propyl. When X is CH$_2$, R$_4$ and R$_5$ may combine to form a benzene ring fused to the 6-membered X-containing ring, i.e., R$_4$ and R$_5$ are defined by the alkatrienyl group =C—CH=CH—CH=.

A particular group of compounds of formula (I) are those wherein X is oxygen and both R$_2$ and R$_3$, and R$_4$ and R$_5$ together are methylenedioxy groups of the formula (II), wherein R$_6$ and R$_7$ are both hydrogen, both alkyl, or combine to form a spiro cyclopentyl or cyclohexyl ring, in particular where R$_6$ and R$_7$ are both alkyl such as methyl. A second group of compounds are those wherein X is CH$_2$ and R$_4$ and R$_5$ are joined to form a benzene ring. A third group of compounds of formula (I) are those wherein both R$_2$ and R$_3$ are hydrogen.

The term "lower alkyl" as used herein refers to branched or straight chain alkyl groups comprising one to ten carbon atoms that are unsubstituted or substituted, e.g., with one or more halogen groups, including, e.g., methyl, ethyl, propyl, isopropyl, n-butyl, t-butyl, neopentyl, trifluoromethyl, pentafluoroethyl and the like.

The term "alkoxy" as used herein refers to RO— wherein R is lower alkyl as defined above. Representative examples of lower alkoxy groups include methoxy, ethoxy, t-butoxy, trifluoromethoxy and the like.

The term "effective amount" as used herein means an amount of a compound of the invention effective to result in the clinically determinable improvement in or suppression of symptoms of post traumatic stress disorder, such as nightmares and intrusions (including intrusive recollections or flashbacks). An improvement in such symptoms includes both a reduction in intensity and frequency of nightmares or intrusions and a complete cessation of nightmares and intrusions for a sustained period.

In a presently particularly preferred embodiment of the invention, the sulfamate is topiramate.

In yet a further aspect of the present invention, pharmaceutical compositions are provided which comprise a compound of the present invention in combination with a pharmaceutically acceptable carrier.

The compounds of formula (I) may be synthesized by the following methods:

(a) Reaction of an alcohol of the formula RCH$_2$OH with a chlorosulfamate of the formula ClSO$_2$NH$_2$ or ClSO$_2$NHR$_1$ in the presence of a base such as potassium a-butoxide or sodium hydride at a temperature of about −20 to 25° C. and in a solvent such as toluene, THF or dimethylformamide wherein R is a moiety of the following formula (III):

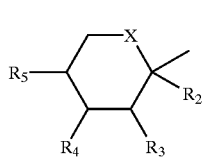

(b) Reaction of an alcohol of the formula $RCH_2OH$ with sulfurylchloride of the formula $SO_2Cl_2$ in the presence of a base such as triethylamine or pyridine at a temperature of about −40° to 25 C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of abut 40° to 25° C. in a solvent such as methylene chloride or acetonitrile to produce a compound of formula (I). The reaction conditions for (b) are also described by T. Tsuchiya et al. in *Tet. Letters* 36:3365 to 3368 (1978).

(c) Reaction of the chlorosulfate $RCH_2OSOCl$ with a metal azide such as sodium azide in a solvent such as methylene chloride or acetonitrile yields an azidosulfate of the formula $RCH_2OSO_2N_3$ as described by M. Hedayatullah in *Tet. Lett. p.* 2455–2458 (1975). The azidosulfate is then reduced to a compound of formula (I) wherein Rlis hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$, and $R_4$ and $R_5$ are identical and are of the formula (II) may be obtained by the method of R. F. Brady in *Carbohydrate Research,* Vol.14, p. 35 to 40 (1970) or by reaction of the trimethylsilyl enol ether of a $R_6COR_7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in *J. Org. Chem.* Vol. 38, No. 22, p. 3935 (1973).

Further, carboxylic acids and aldehydes of the formulae RCOOH and RCHO may be reduced to compounds of the formula $RCH_2OH$ by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I may also be made by the processes disclosed in U.S. Pat. No. 4,513,006 or in U.S. Pat. No. 5,387,700, which are incorporated by reference herein.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygens of the methylenedioxy group (II) are attached on the same side of the 6-membered ring.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds may be used alone or in compositions together with a pharmaceutically acceptable carrier.

For the treatment and/or prophylaxis of the symptoms of post traumatic stress disorder (PTSD), a compound of formula (I) may be employed at a daily dosage in the range of about 10 to 1000 mg, preferably about 15 to about 800 mg, and more preferably about 25 to about 600 mg, that may be administered once, twice or three times a day, or more, for an average adult human. A unit dose may contain, for example, from about 25 to 200 mg of the active ingredient. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1/3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Because of their ease in administration, tablets and capsules represent the most advantageous oral dosage unit form, in which case solid pharmaceutical carriers are obviously employed. Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., diluents, granulating agents, lubricants, binders, disintegrating agents and the like. In the case of capsules, tablets, and pills, the dosage forms may also comprise buffering agents. Tablets and pills can additionally be prepared with sugar or enteric coatings, as is known in the art. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology,* Volume XIV, Academic Press, New York, N.W. (1976), p.33 et seq.

While the compounds of the invention can be administered as the sole active pharmaceutical agent, they can also be used in combination with one or more other agents used in the treatment of post traumatic stress disorder or other psychotic disorders. Representative agents useful in combination with the compounds of the invention for the treatment of PTSD include, for example, sertraline and other psychoactive drugs, such as, for example, serotonin uptake inhibitors, mood stabilizing drugs, and the like.

The compounds of the invention and the other antiinfective agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions which are given at the same time or different times, or the therapeutic agents can be given as a single composition.

The pharmaceutical compositions herein will contain, per dosage unit, e.g., tablet, capsule, powder injection, teaspoonful, suppository and the like from about 25 to about 100 mg of the active ingredient.

The foregoing may be better understood by reference to the following example, which IS provided for illustration and are not intended to limit the scope of the inventive concepts.

EXAMPLE 1

Thirty five (35) patients meeting DSM-IV criteria for chronic post-traumatic stress disorder (PTSD) were selected for a study of the effects of topiramate administration. Of these, 28 had non-hallucinatory PTSD and 6 hallucinatory PTSD. The group with hallucinatory PTSD experienced auditory and/or visual hallucinations containing content specifically associated with identified traumatic events. Whether these were PTSD "flashbacks" or psychotic experiences were at times difficult to ascertain due to fluctuations in reality testing the hallucinations. For this reason, prior to being screened for PTSD, some patients had received psychiatric diagnoses of psychotic disorders despite meeting full diagnostic criteria for PTSD.

Topiramate was added naturalistically to existing pharmacotherapy (see Table 1 for concomitant medications at start of trial), starting at 25 mg|day and increasing whenever possible by 25 to 50 mg/day every 3 to 4 days to clinical response. Target symptoms were DSM-IV PTSD criterion B symptoms of nightmares (N =24) and intrusions (intrusive recollections/flashbacks, N=35) involving re-experiencing of traumas. Definitions of improvement, as assessed from patient self-report, included "partial response" as "definite reduction in intensity and frequency of nightmares or intrusions", and "full response" as "complete cessation of nightmares and intrusions for a sustained period". Following the seminal observations, in order to systematically identify responsive symptoms, the next 17 patients completed a self-report scale, the PTSD Checklist—Civilian Version (PCL-C)15, at baseline and at 4 weeks after starting topiramate. The patients were instructed to complete the PCL-C for experiences corresponding to traumas consistent with DSM-IV criterion A for PTSD. Paired ttest scores for the PCL-C were calculated with Jandel SigmaStat® v. 2.0.

TABLE 1

| Concomitant Medication | | | |
|---|---|---|---|
| | All Patients (N) | Patients with Non-Hallucinatory PTSD (N) | Patients with Hallucinatory PTSD (N) |
| Atypical neuroleptic | 8 | 3 | 5 |
| SSRI | 7 | 6 | 1 |
| Venlafaxine | 3 | 2 | 1 |
| Mirtazepine | 1 | 0 | 1 |

TABLE 1-continued

Concomitant Medication

|  | All Patients (N) | Patients with Non-Hallucinatory PTSD (N) | Patients with Hallucinatory PTSD (N) |
|---|---|---|---|
| Trazodone | 2 | 2 | 0 |
| Nefazodone | 1 | 1 | 0 |
| Bupropion | 2 | 0 | 2 |
| Tricyclic antidepressant | 1 | 1 | 0 |
| MAO inhibitor | 1 | 1 | 0 |
| Stimulant | 4 | 4 | 0 |
| Valproate | 7 | 3 | 4 |
| Lamotrigine | 5 | 5 | 0 |
| Lithium | 2 | 1 | 1 |
| Verapamil | 1 | 1 | 0 |
| Gabapentin | 2 | 2 | 0 |
| Benzodiazepines | 8 | 8 | 0 |
| Methadone | 1 | 0 | 1 |
| Tramadol | 1 | 1 | 0 |
| Donepezil | 2 | 2 | 0 |
| Topiramate monotherapy | 7 | 7 | 0 |

Patient characteristics are summarized in Table 2. Mean age of onset of PTSD symptoms began considerably earlier in patients with bipolar disorder (19±13.6 years) and hallucinatory PTSD (11±4.8 years) than in non-hallucinatory, non-bipolar patients (29±17.4 years). Correspondingly, the mean duration of PTSD symptoms was markedly greater in patients with bipolar disorder (21±13.9 years) or with hallucinations (29±5.6 years) than in non-hallucinatory, non-bipolar patients (14±16.3 years). There was no significant association, however, between duration of symptoms and response to topiramate. Substance abuse, whether past or current at the time of initiation of topiramate, was present in 40% (14/35) of patients. Comorbid mood disorders occurred in all instances, with a bipolar disorder diagnosis in 10/35, major depression in 20/35, and dysthymic disorder in 2135.

TABLE 2

Patient Demographics

|  | All Patients (N = 35) | Patients with Non-Hallucinatory PTSK | | | Hallucinatory PTSD (N = 7) |
|---|---|---|---|---|---|
|  |  | Total (N = 28) | Non-Polar Disorder (N = 20) | Bipolar Disorder (N = 8) |  |
| Age, years |  |  |  |  |  |
| Mean ± SD | 41.1 ± 9.5 | 42.1 ± 9.9 | 43.4 ± 9.9 | 38.9 ± 9.7 | 37.0 ± 7.1 |
| (range) | (21–61) | (21–61) | (21–61) | (21–50) | (26–45) |
| Gender | 26 female/9 male | 22 female/4 male | 16 female/4 male | 6 female/2 male | 4 female/3 male |
| Age of PTSD onset, years |  |  |  |  |  |
| Mean ± SD | 24.1 ± 16.6 | 26.5 ± 16.9 | 29.1 ± 17.4 | 19.1 ± 13.6 | 11.0 ± 4.8 |
| (range) | (3–55) | (3–55) | (3–55) | (5–44) | (6–16) |
| Duration of PTSD, years |  |  |  |  |  |
| Mean ± SD | 18.1 ± 15.3 | 16.1 ± 15.8 | 14.3 ± 16.3 | 21.1 ± 13.9 | 29.0 ± 5.6 |
| (range) | (0–45) | (0–45) | (1–45) | (2–38) | (22–35) |
| Other diagnoses (N) |  |  |  |  |  |
| Bipolar disorder | 10 | 8 | 0 | 8 | 2 |
| Major depressive disorder | 20 | 15 | 15 | 0 | 5 |
| Substance abuse (N) |  |  |  |  |  |
| Current | 2 | 1 | 1 | 0 | 1 |
| Past | 12 | 8 | 5 | 3 | 4 |

The primary trauma, as reflected in nightmares and intrusions, most commonly included physical assault and unwanted sexual experience (see Table 3). There were no apparent differences in types of primary trauma across patient groupings.

TABLE 3

Primary Trauma Reflected in Nightmares and Intrusions

|  | All Patients (N) | Patients with Non-Hallucinatory PTSD (N) | Patients with Hallucinatory PTSD (N) |
|---|---|---|---|
| Physical assault | 11 | 7 | 4 |
| Sexual assault | 5 | 5 | 0 |
| Unwanted sexual experience | 5 | 3 | 2 |
| Sudden unexpected death of someone close | 3 | 3 | 0 |
| Serious injury or death | 2 | 2 | 0 |
| Transportation accident | 2 | 2 | 0 |
| Severe human suffering | 2 | 2 | 0 |
| Weapon assault | 1 | 0 | 1 |
| Combat (military or civilian exposure in war zone) | 1 | 1 | 0 |
| Sudden violent death | 1 | 1 | 0 |

TABLE 3-continued

Primary Trauma Reflected in Nightmares and Intrusions

| | All Patients (N) | Patients with Non-Hallucinatory PTSD (N) | Patients with Hallucinatory PTSD (N) |
|---|---|---|---|
| Other (death threats to patient and family, etc) | 2 | 2 | 0 |

Response assessment, summarized in Table 4, used the Last Observation Carried Forward (LOCF) method, which includes all patients who entered the trial and their last reported condition while under active treatment. Overall, topiramate suppressed nightmares in 79% of patients (14/28 fully; 5/28 partially), and intrusions in 86% (22/35 fully; 8/35 partially). Globally (i.e., in terms of suppression of both nightmares and intrusions), 22 patients (63%) reported a full response and 8 patients (23%) a partial response. Five patients discontinued without response, 1 at 5 days, and the remaining 4 after 4 weeks. The non-hallucinatory subgroup achieved a higher response rate (full: 79%; full/partial: 89%). All full responses occurred in the non-hallucinatory subgroup. Benefit usually occurred within 2 to 3 days of reaching an effective dose. A full response to topiramate was reported for 10 patients within 1 week of treatment, and for 3 additional patients by the third week of treatment.

TABLE 4

Response to Topiramate

| | | Patients with Non-Hallucinatory PTSD | | | |
|---|---|---|---|---|---|
| | All Patients (N = 35) | Total (N + 28) | Non-Bipolar Disorder (N = 20) | Bipolar Disorder (N = 8) | Patients with Hallucinatory PTSD (N = 7) |
| Suppression of nightmares (N = 24) | 79% (19/24) | 84% (16/19) | 85% (11/13) | 83% (5/6) | 60% (3/5) |
| Partial | 5 | 2 | 1 | 1 | 3 |
| Full | 14 | 14 | 10 | 4 | 0 |
| Suppression of intrusions (N = 35) | 86% (30/35) | 89% (25/28) | 90% (18/20) | 88% (7/8) | 71% (5/7) |
| Partial | 8 | 3 | 2 | 1 | 5 |
| Full | 22 | 22 | 16 | 6 | 0 |
| Time to onset of response, mean ± SD (median) | | | | | |
| Partial, days | 10.9 ± 13.1 (4.0) | 10.3 ± 12.7 (4.0) | 8.6 ± 12.4 (3.5) | 17.3 ± 13.5 (17.0) | 12.6 ± 15.7 (7.0) |
| Full, days | 35.3 ± 48.6 (8.0) | 35.3 ± 48.6 (8.0) | 32.1 ± 44.1 (10.0) | 43.3 ± 62.5 (6.0) | — |
| Dosage of topiramate, mean ± SD (median) | | | | | |
| Partial, mg/day | 41.7 ± 31.7 (25.0) | 32.8 ± 17.0 (25.0) | 26.9 ± 11.2 (25.0) | 58.3 ± 14.4 (50.0) | 70.0 ± 51.2 (75.0) |
| Full, mg/day | 78.6 ± 113.8 (50.0) | 78.6 ± 113.8 (50.0) | 48.3 ± 25.4 (50.0) | 154.2 ± 200.9 (37.5) | — |

Response was also assessed in 17 patients who completed the PCL-C prior to topiramate therapy and at Week 4 of treatment: mean total PCL-C scores were 60±10.4 at baseline and 39±10.5 at Week 4 (instrument range: 17 to 85, threshold for active PTSD=50, p=002, paired t-test). Adjusting the baseline score by subtracting by 17 to set the score for no PTSD symptoms to zero, there was a 48% reduction (59.8 to 38.8)/(59.8−17) in total score. Subscale score reductions were similar for criterion B (re-experiencing), criterion C (avoidance), and criterion D (hyperarousal) symptoms: 60%, 49%, and 42%, respectively.

Mean/median time to onset of response is shown in FIG. 1 by patient group. For all patients combined, mean time to onset of partial response for either nightmares or intrusions was 11±13.1 days with a median of 4.0 days. For non-hallucinatory patients, mean time of onset was 10±12.7 days with a median of 4.0 days. For hallucinatory PTSD patients, mean time was 13±15.7 days with a median of 7.0 days. Mean time to onset of a full response for both nightmares and intrusions, which was seen only in non-hallucinatory patients, was 35±48.6 days, with a median of 8.0 days. The skewing of time-to-response reflects naturalistic variations in days between clinical encounters and individual differences in effective dosage. The longest duration of treatment has been 119 weeks.

Evidence of response was seen at relatively low mean doses of topiramate: response was seen in 95% of partial responders at a dosage of 75 mg/day or less. Response was seen in 91% of full responders at a dosage of 100 mg/day or less. The threshold dosage for partial response for the entire sample was 42±31.7 mg/day (median=25.0 mg/day). Lowest threshold doses were attained by non-hallucinatory, non-bipolar patients (30±11.2 mg/day, median=25.0 mg/day) and highest doses by hallucinatory PTSD patients (70.0±51.2 mg/day, median=75.0 mg/day) followed by non-hallucinatory, bipolar patients (58±14.4 mg/day, median= 50.0 mg/day). Globally, the mean dose required for a full response was 79±113.8 mg/day, median=50.0 mg/day), with a markedly lower dose for non-bipolar (48±25.4 mg/day, median=50.0 mg/day) compared with bipolar patients (154±200.9 mg/day, median=37.5 mg/day). Four of seven bipolar responders displayed a full response only, thereby lowering the median full response value below the partial response value.

Thirteen patients eventually discontinued treatment: 9 due to side effects (urticaria [N=1], eating cessation [N=2], ocular and limb paresthesias [N=1], severe headaches [N=1], overstimulation/panic [N=2], emergent suicidal ideation [N=1], and memory concerns [N=1]) and 4 for other reasons (patient choice [N=1], lack of relapse upon medication interruption [N=2], lack of efficacy [N=1]). Five of the discontinuers had experienced full symptom remission prior to discontinuation and 3 additional patients reported partial response.

The present invention represents the first recognition of the effect of topiramate in PTSD. Topiramate has been shown to be markedly and rapidly effective as add-on or monotherapy in patients meeting DSM-IV criteria for PTSD with prominent criterion B symptoms of trauma-related nightmares or intrusive memories/flashbacks. A high response rate occurred (full: 63%; full/partial: 86%) independent of non-psychotic psychiatric comorbidities and concomitant medication. The type of PTSD presentation, however, affected response rates, insofar as the non-hallucinatory subgroup achieved a higher response rate (full: 79%; full/partial: 89%) than the hallucinatory group (full: 0%; partial: 83%). Topiramate demonstrated a rapid onset of action, often within days and often at doses considerably lower than those typically used for antiepileptic therapy. Experience to date suggests that topiramate markedly suppresses criterion B (re-experiencing) symptoms of PTSD and, although less investigated, criterion C (avoidance) and criterion D (hyperarousal) symptoms as well.

Topiramate posed no safety issues in the study reported in this example. Discontinuation due to medication-associated side effects, such as nausea and memory concerns, may have been due to the presence of other medications, to medication interactions, or to individual variation in time needed to accommodate to initial side effects. Subsequent to discontinuation of topiramate, the patient who experienced urticaria continued to complain of unrelated episodes of urticaria. Typical side effects such as dizziness, nausea, or paresthesias were usually transient and, with the exception of nausea and one instance of late-onset headache, did not result in discontinuation. When they occurred, side effects were easily managed by dosage reduction or a brief hiatus in administration. In general, topiramate appeared well tolerated in this population and perhaps even better tolerated in the absence of other medications.

In accordance with the present invention, topiramate and its related sulfamate derivatives described herein appear to be the first rapidly acting therapeutic agents for those symptoms of PTSD which. are often most distressing for patients and least consistently responsive to conventional medication such as antidepressants and benzodiazepines. These data, combined with what is known about topiramate from studies of epilepsy and other psychiatric disorders, suggest that topiramate will be well tolerated over time, have lower toxicity than other anticonvulsants such as carbamazepine and valproate, and obviate the need for laboratory monitoring.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for treating post traumatic stress disorder comprising administering to a mammal afflicted therewith a therapeutically effective amount of a compound of the formula I:

$$\text{(I)}$$

wherein
X is $CH_2$ or oxygen;
$R_1$ is hydrogen or alkyl; and
$R_2$, $R_3$, $R_4$ and $R_5$ are independently hydrogen or lower alkyl and, when X is $CH_2$, $R_4$ and $R_5$ may be alkene groups joined to form a benezene ring and, when X is oxygen, $R_2$ and $R_3$ and/or $R_4$ and $R_5$ together may be a methylenedioxy group of the following formula (II):

$$\text{(II)}$$

wherein $R_6$ and $R_7$ are the same or different and are hydrogen, lower alkyl or are alkyl and are joined to form a cyclopentyl or cyclohexyl ring;

or a pharmacologically acceptable acid addition salt thereof, alone or in association with a pharmaceutically acceptable carrier.

2. The method of claim 1 wherein the compound of formula I is topiramate.

3. The method of claim 1, wherein the therapeutically effective amount is from about 10 to 1000 mg.

4. The method of claim 1, wherein the amount is of from about 25 to 600 mg.

5. A method for treating a mammalian patient comprising determining that the patient suffers from post traumatic stress disorder, and then administering to the patient a therapeutically effective amount of a compound of the formula I:

$$\text{(I)}$$

wherein
X is $CH_2$ or oxygen;
$R_1$ is hydrogen or alkyl; and
$R_2$, $R_3$, $R_4$ and $R_5$ are independently hydrogen or lower alkyl and, when X is $CH_2$, $R_4$ and $R_5$ may be alkene groups joined to form a benezene ring and, when X is oxygen, $R_2$ and $R_3$ and/or $R_4$ and $R_5$ together may be a methylenedioxy group of the following formula (II):

$$\text{(II)}$$

wherein R6 and $R_7$ are the same or different and are hydrogen, lower alkyl or are alkyl and are joined to form a cyclopentyl or cyclohexyl ring;

or a pharmacologically acceptable acid addition salt thereof, alone or in association with a pharmaceutically acceptable carrier.

6. The method of claim 5 wherein the compound of formula I is topiramate.

7. The method of claim 5, wherein the therapeutically effective amount is from about 10 to 1000 mg.

8. The method of claim 5, wherein the amount is from about 25 to 600 mg.

* * * * *

UNITED STATES PATENT AND TRADEMARK OFFICE
CERTIFICATE OF CORRECTION

PATENT NO.     : 6,486,198 B1
DATED          : November 26, 2002
INVENTOR(S)    : J. Berlant It is certified that error appears in the above-identified patent and that said Letters Patent is hereby corrected as shown below:

Title page,
Item [56], References Cited, OTHER PUBLICATIONS, insert in appropriate order:

-- OTHER PUBLICATIONS
Martin, R., et al., "Cognitive Effects of Topiramate, Gabapentin, and Lamotrigine in Healthy Young Adults," *Neurology* 52(2):321-327, Feb. 1999, Database CA on STN, Chemical Abstracts Service (Columbus, Ohio, USA) No. 130:332700. --

Column 1,
Line 7, "This application claims" should read -- This application is a 371 of PCT/US00/14593, filed May 26, 2000, which claims --
Lines 36-37, "reexperi-
              encing" should read -- re-experi-
              encing --
Line 61, "4,5.13,006," should read -- 4,513,006, --

Column 2,
Line 43, "Topirarnate Y P" should read -- Topiramate YP --

Column 8,
Line 38, "mglday" should read -- mg/day --
Line 53, "ttest" should read -- t-test --

Column 9,
Line 39, "2135." should read -- 2/35. --

Column 12,
Line 21, "p=002," should read -- p=.002, --

UNITED STATES PATENT AND TRADEMARK OFFICE
CERTIFICATE OF CORRECTION

PATENT NO.     : 6,486,198 B1
DATED          : November 26, 2002
INVENTOR(S)    : J. Berlant It is certified that error appears in the above-identified patent and that said Letters Patent is hereby corrected as shown below:

Column 13,
Line 42, "PTSD which." should read -- PTSD which --

Column 14,
Line 25, "is of from" should read -- is from --
Line 54, "R6" should read -- $R_6$ --

Signed and Sealed this

Fifteenth Day of July, 2003

JAMES E. ROGAN
*Director of the United States Patent and Trademark Office*